(12) United States Patent
Sakamoto et al.

(10) Patent No.: US 12,678,530 B2
(45) Date of Patent: Jul. 14, 2026

(54) AIR PURIFIER AND METHOD FOR CONTROLLING THE SAME

(71) Applicant: SHARP KABUSHIKI KAISHA, Sakai City (JP)

(72) Inventors: Masafumi Sakamoto, Sakai (JP); Tatsufumi Atsumi, Sakai (JP); Noriaki Taguchi, Sakai (JP)

(73) Assignee: SHARP KABUSHIKI KAISHA, Sakai City (JP)

( * ) Notice: Subject to any disclaimer, the term of this patent is extended or adjusted under 35 U.S.C. 154(b) by 545 days.

(21) Appl. No.: 18/118,470

(22) Filed: Mar. 7, 2023

(65) Prior Publication Data

US 2023/0285627 A1 Sep. 14, 2023

(30) Foreign Application Priority Data

Mar. 9, 2022 (JP) ................................. 2022-035978

(51) Int. Cl.
A61L 9/20 (2006.01)
(52) U.S. Cl.
CPC .......... A61L 9/205 (2013.01); *A61L 2209/111* (2013.01); *A61L 2209/12* (2013.01); *A61L 2209/14* (2013.01)
(58) Field of Classification Search
CPC ...................................................... A61L 9/205
See application file for complete search history.

(56) References Cited

U.S. PATENT DOCUMENTS

| | | |
|---|---|---|
| 2012/0219459 A1 | 8/2012 | Nakatani |
| 2019/0263226 A1* | 8/2019 | Gruenbeck ............. A61L 9/205 |
| 2021/0060199 A1 | 3/2021 | Somei et al. |

FOREIGN PATENT DOCUMENTS

| | | |
|---|---|---|
| EP | 0798143 A1 | 10/1997 |
| JP | H09-313882 A | 12/1997 |
| JP | 2011-092873 A | 5/2011 |
| JP | 2021-037285 A | 3/2021 |
| JP | 2021-046997 A | 3/2021 |

* cited by examiner

*Primary Examiner* — Kevin Joyner
(74) *Attorney, Agent, or Firm* — ScienBiziP, P.C.

(57) ABSTRACT

The air purifier is provided with a housing having an air intake port and an exhaust port, a filter unit including a photocatalytic filter and housed in a unit housing section within the housing, a light source that irradiates the photocatalytic filter with light, an air blowing fan that generates an air flow passing through the unit housing section, and a contamination sensor provided between the photocatalytic filter and the air blowing fan. In a case where a controller determines that organic substances excessively adheres to the photocatalytic filter on the basis of detection values of the contamination sensor, it drives the light source at the maximum light quantity and drives the air blowing fan at the minimum air speed to refresh the photocatalytic filter.

12 Claims, 16 Drawing Sheets

CRITERION OF CONTAMINATION LEVEL

| CONTAMINATION LEVEL | CONTAMINATION VALUE |
|---|---|
| 0 | 0.65 OR MORE AND ONE OR LESS |
| 1 | 0.35 OR MORE AND LESS THAN 0.65 |
| 2 | ZERO OR MORE AND LESS THAN 0.35 |

FIG. 10

INFORMATION ON OPERATING CONTROL

| | OPERATING MODE | | | |
|---|---|---|---|---|
| | SILENT | NORMAL | STRONG | REFRESH |
| ILLUMINANCE | 60 | 60 | 80 | 100 |
| AIR SPEED | 25 | 75 | 100 | 25 OR LESS |

MEMORY MAP OF RAM 106  300

PROGRAM STORAGE AREA — 302

OPERATION DETECTION PROGRAM — 302a

FAN CONTROL PROGRAM — 302b

LIGHT SOURCE CONTROL PROGRAM — 302c

CONTAMINATION CHECK PROGRAM — 302d

DETERMINATION PROGRAM FOR PERFORMING CHECK — 302e

DATA STORAGE AREA — 304

OPERATION DATA — 304a

OPERATING MODE DATA — 304b

FIRST CONTAMINATION VALUE DATA — 304c

SECOND CONTAMINATION VALUE DATA — 304d

CHECK VALUE DATA — 304e

FIG. 16

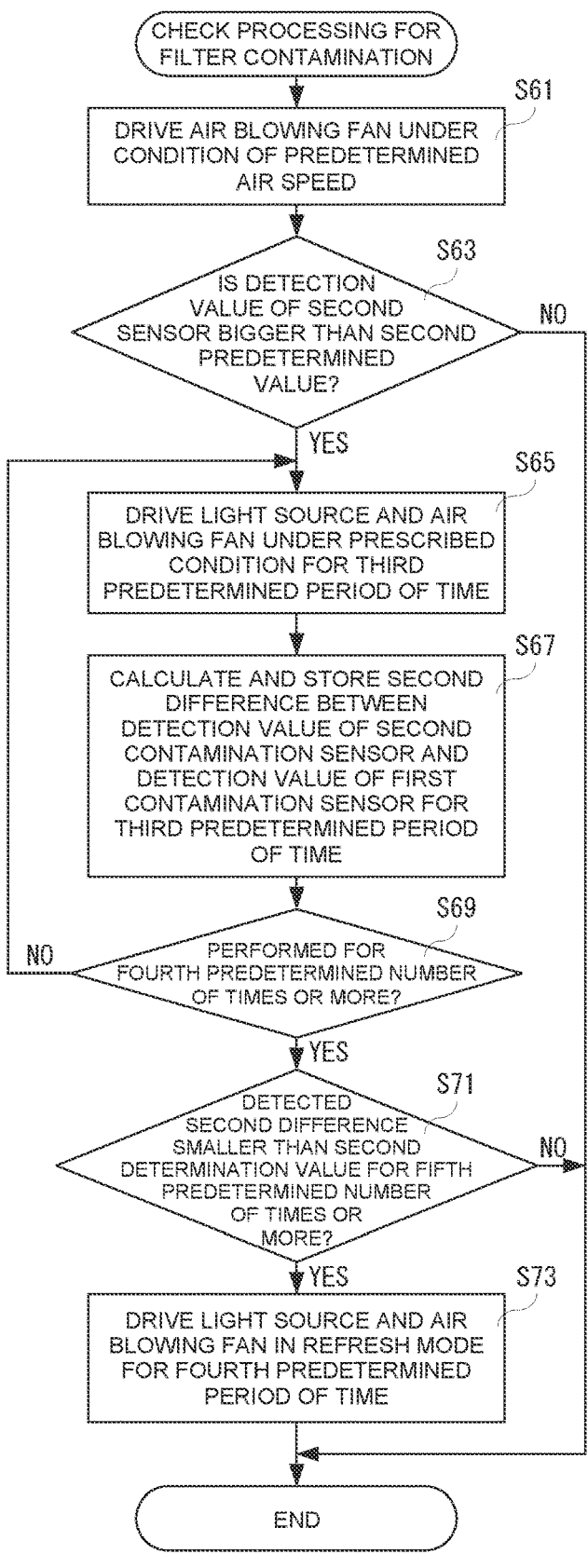

CHECK PROCESSING FOR
FILTER CONTAMINATION

S61
DRIVE AIR BLOWING FAN UNDER
CONDITION OF PREDETERMINED
AIR SPEED

S63
IS DETECTION
VALUE OF SECOND
SENSOR BIGGER THAN SECOND
PREDETERMINED
VALUE?

NO

YES

S65
DRIVE LIGHT SOURCE AND AIR
BLOWING FAN UNDER PRESCRIBED
CONDITION FOR THIRD
PREDETERMINED PERIOD OF TIME

S67
CALCULATE AND STORE SECOND
DIFFERENCE BETWEEN
DETECTION VALUE OF SECOND
CONTAMINATION SENSOR AND
DETECTION VALUE OF FIRST
CONTAMINATION SENSOR FOR
THIRD PREDETERMINED PERIOD
OF TIME

S69
PERFORMED FOR
FOURTH PREDETERMINED NUMBER
OF TIMES OR MORE?

NO

YES

S71
DETECTED
SECOND DIFFERENCE
SMALLER THAN SECOND
DETERMINATION VALUE FOR FIFTH
PREDETERMINED NUMBER
OF TIMES OR
MORE?

NO

YES

S73
DRIVE LIGHT SOURCE AND AIR
BLOWING FAN IN REFRESH MODE
FOR FOURTH PREDETERMINED
PERIOD OF TIME

END

AIR PURIFIER AND METHOD FOR CONTROLLING THE SAME

BACKGROUND OF THE INVENTION

Field of the Invention

The present disclosure relates to an air purifier and a method for controlling the same, in particular, to the air purifier and the method for controlling the same, which purifies air, for example, using a photocatalytic filter that carries a photocatalyst.

Description of the Background Art

There is an air purifier (photocatalytic device) provided with a housing, a filter unit (photocatalytic unit) that includes a flat photocatalytic filter (photocatalytic sheet) and is disposed in the housing, a light source (light) for providing light to the photocatalytic filter, and an air blowing fan for blowing air over a surface of the photocatalytic filter.

Since the conventional air purifier described above employs a flat photocatalytic filter, for the purpose of achieving sufficient decomposition performance of organic substances (that is to say, air purification performance), there has been an issue that the photocatalytic filter has to increase in size, which can cause the air purifier to grow larger. There has also been an issue that in a case where a large amount of organic substances to be purified are contained in the air and are excessively adhered to the photocatalytic filter, decomposition efficiency of the organic substances can be degraded.

Therefore, a main object of the present disclosure is to provide a new air purifier.

Another object of the present disclosure is to provide an air purifier that can effectively purify air and can be reduced in size.

SUMMARY OF THE INVENTION

The first disclosure is an air purifier comprising an air blowing fan, a photocatalytic filter that carries a photocatalyst, a light source that irradiates the photocatalytic filter, and a first sensor that is disposed on a downstream side of the photocatalytic filter in an air blowing direction by the air blowing fan and detects organic substances contained in the air, wherein the air purifier is provided with a controller that is capable of causing the light source to emit light at the maximum light quantity, which is the largest one of light quantities emitted during operation of the air purifier, and driving the air blowing fan at the minimum air speed that is the slowest one of the speeds of air generated during operation of the air purifier, to refresh the photocatalytic filter.

The second disclosure is dependent on the first disclosure, wherein in a case where the light source is caused to emit light at two different light quantities, the controller performs first check processing to check an amount of organic substance adhering to the photocatalytic filter from a difference in values detected by the first sensor and determines on the basis of a result of the first check processing whether it is necessary to refresh the photocatalytic filter.

The third disclosure is dependent on the second disclosure, wherein the controller detects, in the first check processing, a first difference between a first detection value of the first sensor which is an average value of detection results corresponding to a first predetermined number of times obtained by driving the light source at a first light quantity for a first predetermined period of time and a second detection value of the first sensor which is an average value of detection results corresponding to the first predetermined number of times obtained by driving the light source at a second light quantity larger than the first light quantity for the first predetermined period of time, causes the light source to emit light at the maximum light quantity that is larger than the second light quantity, and drives the air blowing fan at the minimum air speed to refresh the photocatalytic filter in a case where the first difference is smaller than a first determination value.

The fourth disclosure is dependent on the second disclosure or the third disclosure, wherein the first check processing is performed in a case where the detection value of the first sensor is equal to or more than a first predetermined value in a state where the light source is turned off.

The fifth disclosure is dependent on any one of the second disclosure to the fourth disclosure, wherein the first difference is calculated for a second predetermined number of times that is twice or more, and the controller refreshes the photocatalytic filter in a case where the first difference smaller than the first determination value has been detected for a third predetermined number of times.

The sixth disclosure is dependent on the first disclosure, further comprising a second sensor that detects organic substances contained in the air on an upstream side of the photocatalytic filter in the air blowing direction by the air blowing fan of the photocatalytic filter, wherein the controller performs second check processing for checking the photocatalytic filter contamination from a second difference between the detection value of the first sensor and the detection value of the second sensor in a state where the light source is caused to emit light at a predetermined light quantity on the basis of the detection value of the second sensor.

The seventh disclosure is dependent on the sixth disclosure, wherein the controller refreshes the photocatalytic filter by emitting the light source at the maximum light quantity and driving the air blowing fan at the minimum air speed in a case where the second difference is smaller than a second determined value.

The eighth disclosure is dependent on the sixth or seventh disclosure, wherein the second check processing is performed in a case where the detection value of the first sensor or the second sensor in the state where the light source is turned off is equal to or more than the first predetermined value.

The ninth disclosure is dependent on any one of the sixth disclosure to the eighth disclosure, wherein the second difference is calculated for a fourth predetermined number of times that is twice or more, and the controller refreshes the photocatalytic filter in a case where the second difference smaller than the second determination value has been detected for a third predetermined number of times.

The tenth disclosure is dependent on the first disclosure, wherein the controller refreshes the photocatalytic filter when an air purification operating is completed.

The eleventh disclosure is dependent on the tenth disclosure, wherein the controller decides a time to refresh the photocatalytic filter in accordance with an air purification operating time.

The twelfth disclosure is a program for controlling an air purifier comprising an air blowing fan, a photocatalytic filter that carries a photocatalyst, a light source that irradiates the photocatalytic filter, and a sensor that is disposed on a downstream side of the photocatalytic filter in an air blowing direction by the air blowing fan and detects organic substances contained in the air, wherein in a case where a predetermined condition is met, a processor of the air purifier is caused to perform steps of causing the light source to emit light at the maximum light quantity that is the largest one of the light quantities emitted during operation of the air purifier, and driving the air blowing fan at the minimum air speed that is the slowest one of the speeds of air generated during operation of the air purifier thereby to refresh the photocatalytic filter.

The thirteenth disclosure is a method for controlling an air purifier comprising an air blowing fan, a photocatalytic filter that carries a photocatalyst, a light source that irradiates the photocatalytic filter, and a sensor that is disposed on a downstream side of the photocatalytic filter in an air blowing direction by the air blowing fan and detects organic substances contained in the air, wherein in a case where a predetermined condition is met, the method is performed by causing the light source to emit light at the maximum light quantity that is the largest one of the light quantities emitted during operation of the air purifier and driving the air blowing fan at the minimum air speed that is the slowest one of the speeds of air generated during operation of the air purifier to refresh the photocatalytic filter.

According to the present disclosures, the photocatalytic filter is refreshed, thereby resulting in possibly decomposing organic substances that have excessively adhered to the photocatalytic filter to restore the decomposition efficiency of the organic substances that have been degraded. Therefore, the air can be purified efficiently. In addition, the photocatalytic filter can be refreshed at an appropriate time.

The above-mentioned objects, other objects, features, and advantages according to the present disclosures will be made clearer from detailed descriptions of embodiments described below with reference to the drawings.

BRIEF DESCRIPTION OF THE DRAWINGS

FIG. 8 is a graph illustrating temporal changes in concentration of organic substances in the air in a case of employing photocatalytic filters with a different adhesion amount of organic substances.

FIG. 9 is a table illustrating a criterion of a contamination level.

FIG. 10 is a table illustrating information on an operating control.

FIG. 16 is a flow diagram illustrating check processing for filter contamination by a CPU of the air purifier according to the second embodiment.

DESCRIPTION OF THE PREFERRED EMBODIMENTS

First Embodiment

Figure 1:
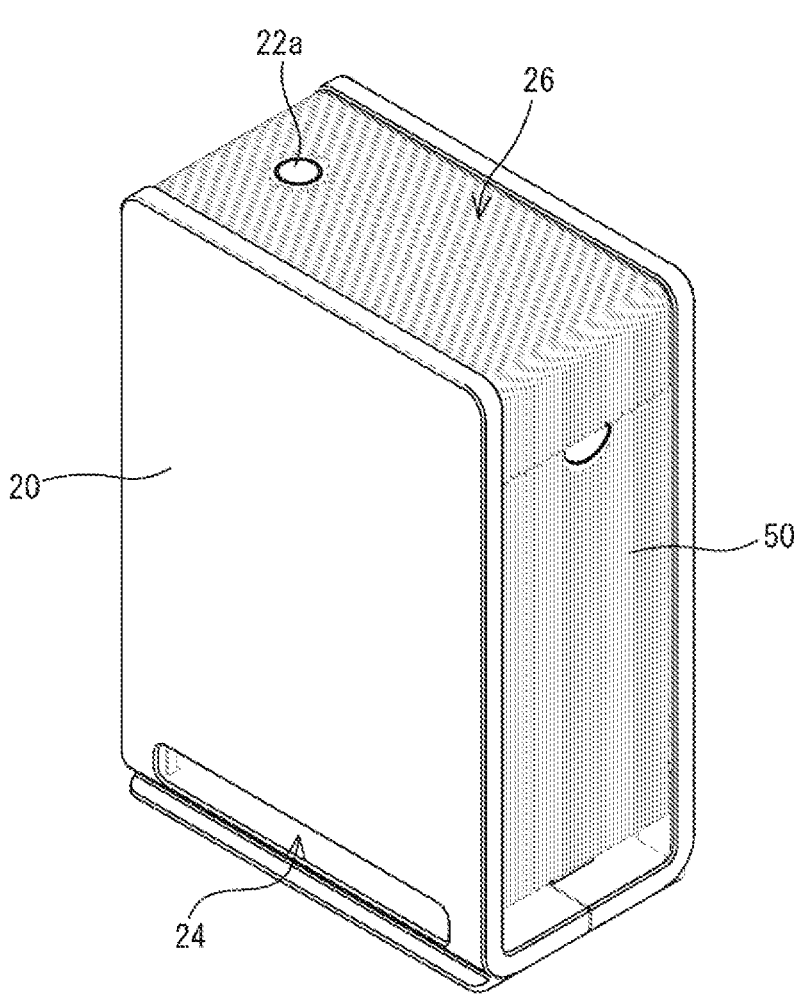
FIG. 1 is a perspective diagram illustrating an air purifier according to a first embodiment according to the present disclosures.
Figure 2:
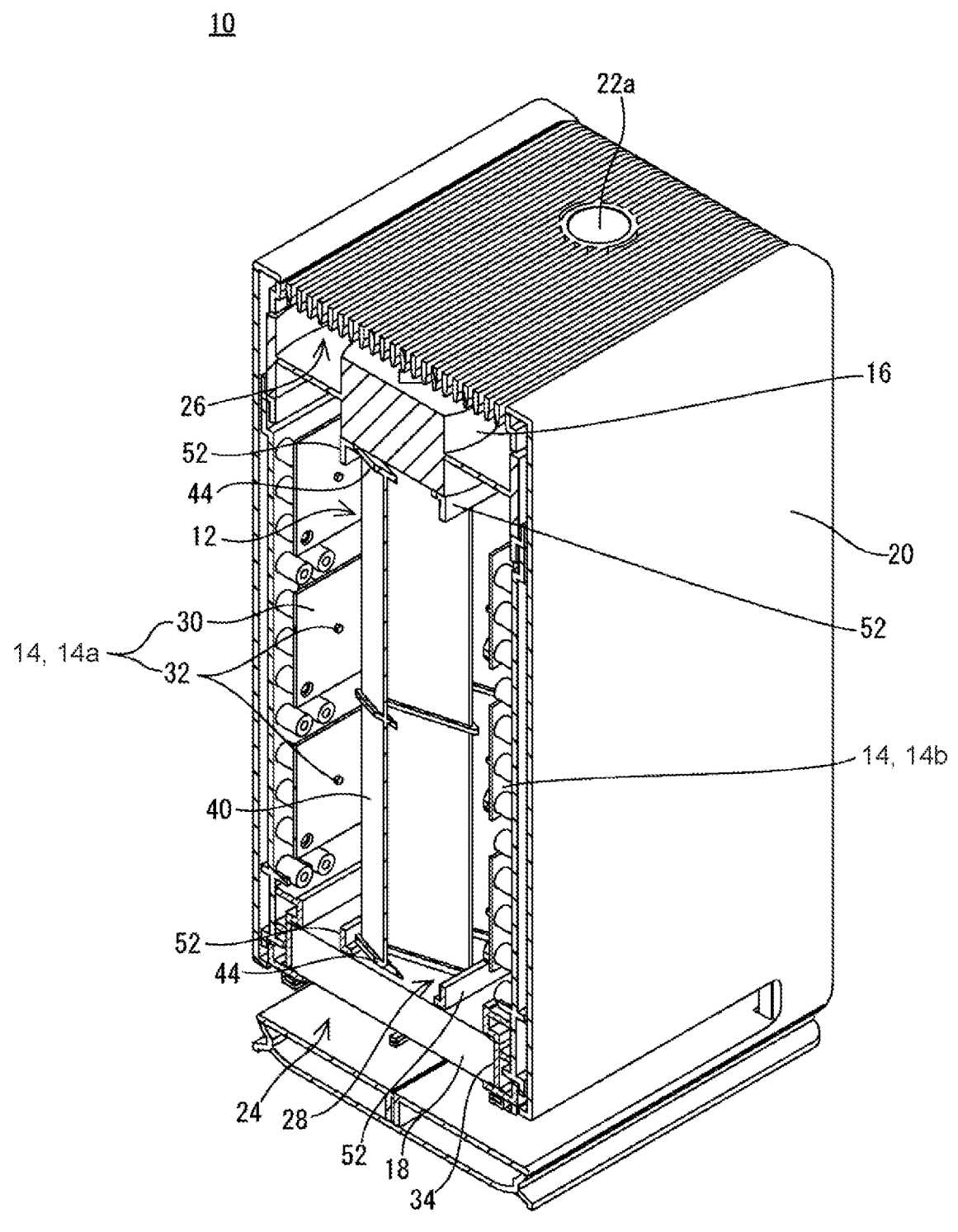
FIG. 2 is a vertical cross-sectional diagram illustrating an inner structure of the air purifier.

With reference to FIG. 1 and FIG. 2, an air purifier 10 of a first embodiment according to the present disclosures is a device that performs sterilization and deodorization using a photocatalytic filter 40 that carries a photocatalyst. As described in detail below, the air purifier 10 decomposes organic substances (organic compounds) adhering to the photocatalytic filter 40 by irradiating the photocatalytic filter 40 with light in addition to flowing the air taken from the outside along a main surface (surface) of the photocatalytic filter 40, thereby performing sterilization and deodorization. Hereinafter, a configuration of the air purifier 10 will be described in detail.

Figure 3:
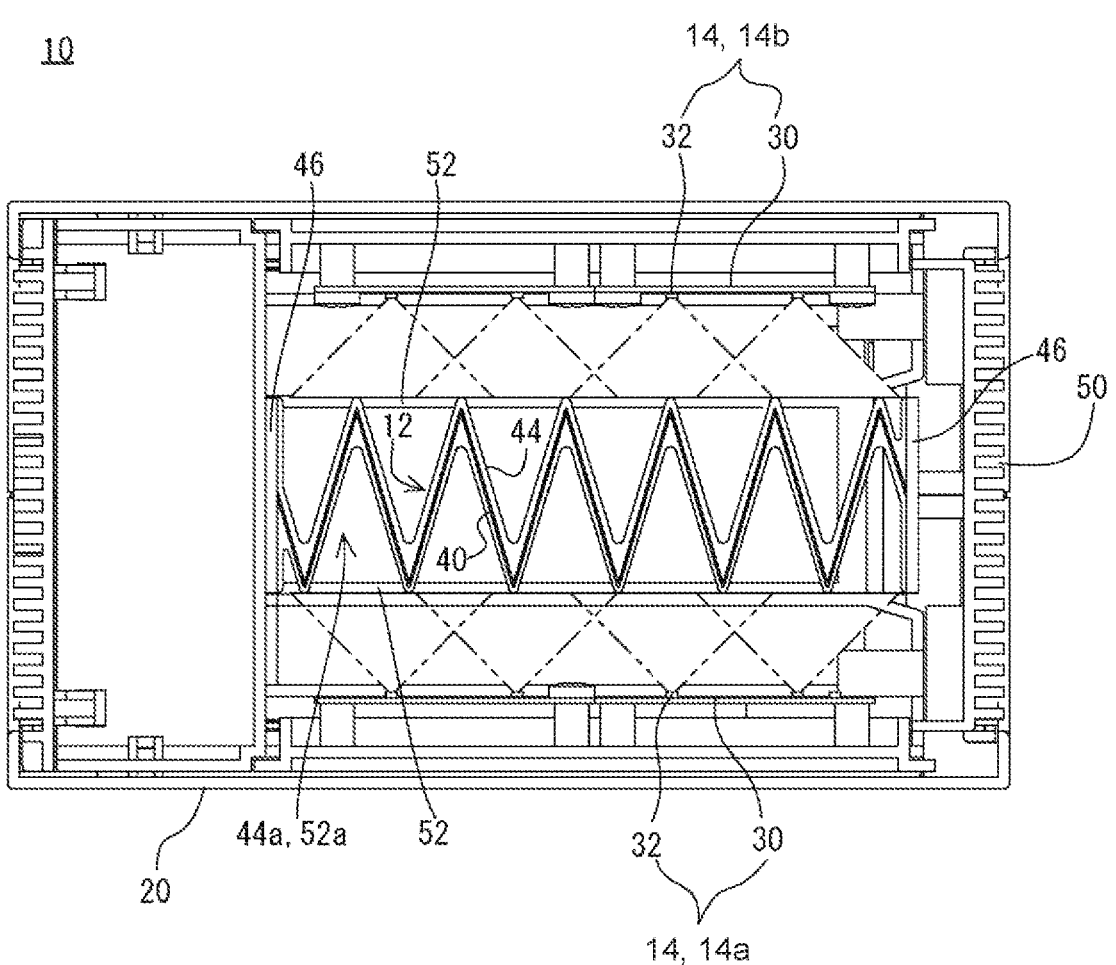
FIG. 3 is a transverse cross-sectional diagram illustrating the inner structure of the air purifier.

As illustrated in FIG. 1 to FIG. 3, the air purifier 10 is provided with a filter unit 12 including the photocatalytic filter 40 and a holding frame 42, a light source 14, an air blowing fan 16, an activated carbon filter 18, and a controller 100 (refer to FIG. 7), which are built into a housing 20 in a predetermined arrangement manner. The controller 100 includes a CPU 102 and a memory (106, 108) and controls operating of each component (the light source 14, the air blowing fan 16, and the like) of the air purifier 10 on the basis of an input operation to an operation section 22 including a power button 22a.

For example, the air purifier 10 can operate in three operating modes (according to the first embodiment, a silent mode, a normal mode, and a strong mode) in a case of purifying air, and the controller 100 can switch the operating modes in accordance with user's input operation (for convenience of explanation, the operating mode can be hereinafter referred to as "operating mode for air purification"). However, in the operating mode for air purification, the silent mode is selected when a power is turned on, and the normal mode or the strong mode can be selected in accordance with user's operation. Furthermore, in the normal mode or the strong mode, the silent mode can be selected in accordance with user's operation. Alternatively, the operating mode for air purification may be set automatically.

As an example, in a case where the operating mode for air purification is set in the silent (weak) mode, the light source 14 is driven at a duty ratio of 60%, and the air blowing fan 16 is driven at a duty ratio of 25%. In a case where the operating mode for air purification is set in the normal (medium) mode, the light source 14 is driven at a duty ratio of 60%, and the air blowing fan 16 is driven at a duty ratio of 75%. Furthermore, in a case where the operating mode for air purification is set in the strong mode, the light source 14 is driven at a duty ratio of 80%, and the air blowing fan 16 is driven at a duty ratio of 100%.

Here, the light source 14 is turned off at a duty ratio of 0% and emits light at the maximum light quantity at a duty ratio of 100%. The air blowing fan 16 is driven so as to achieve the minimum air speed at a duty ratio of 25% or less (including 0%) and to achieve the maximum air speed at a duty ratio of 100%. In the present specification, the largest one of the light quantities emitted during operation of the air purifier 10 may be described as the maximum light quantity for convenience. In addition, the slowest one of the speeds of air generated during operation of the air purifier 10 may be described as the minimum air speed for convenience.

The housing 20 is formed in a rectangular shape. An air intake port 24 is disposed at a bottom of the housing 20, and an exhaust port 26 is disposed at a top of the housing 20. In addition, a unit housing section 28 is disposed at a center of the housing 20. The filter unit 12 is vertically housed (mounted) into this unit housing section 28. A specific structure of the filter unit 12 will be descried in detail below.

The light source 14 includes a substrate 30 and a plurality of LEDs 32 (light emitting diodes) disposed on a surface of the substrate 30 in a dispersed manner, and is disposed so as to be opposed to a main surface of the photocatalytic filter 40. In the present embodiment, the light sources 14 includes a first light source 14a provided so as to be opposed to one main surface of the photocatalytic filter 40 and a second light source 14b provided so as to be opposed to the other main surface of the photocatalytic filter 40. In other words, the light sources 14 are provided on both sides of the filter unit 12 in a thickness direction and can irradiate each of the main surfaces of the photocatalytic filter 40 with light. For example, twelve LEDs 32 are provided on each of the first light source 14a and the second light source 14b.

The air blowing fan 16 is provided at an upper section of the housing 20, that is to say, between the exhaust port 26 and the unit housing section 28 (that is to say, the filter unit 12) to generate a flow of air (air flow) flowing upward from the air intake port 24 through the unit housing section 28 toward the exhaust port 26. In other words, the air that has been taken from the air intake port 24 into the housing 20 by driving the air blowing fan 16 flows upward through the unit housing section 28 and then, is discharged from the exhaust port 26 to an outside of the housing 20. An axial fan such as a propeller fan and a known fan such as a centrifugal fan may be applied as the air blowing fan 16.

Additionally, an activated carbon filter housing section 34 is provided at a lower section of the housing 20, that is to say, between the air intake port 24 and the unit housing section 28. The activated carbon filter 18 is horizontally housed into this activated carbon filter housing section 34 so as to cover the air intake port 24. In other words, the air that has been taken from the air intake port 24 into the housing 20 passes through the activated carbon filter 18 in a thickness direction (that is to say, passes an inside of the activated carbon filter 18) and then, flows into the unit housing section 28. The activated carbon filter 18 is a filter in which activated carbon is carried on a porous base material such as a nonwoven fabric made of a synthetic resin and absorbs odor components such as ammonia and hydrogen sulfide contained in the air to be removed.

Figure 4:
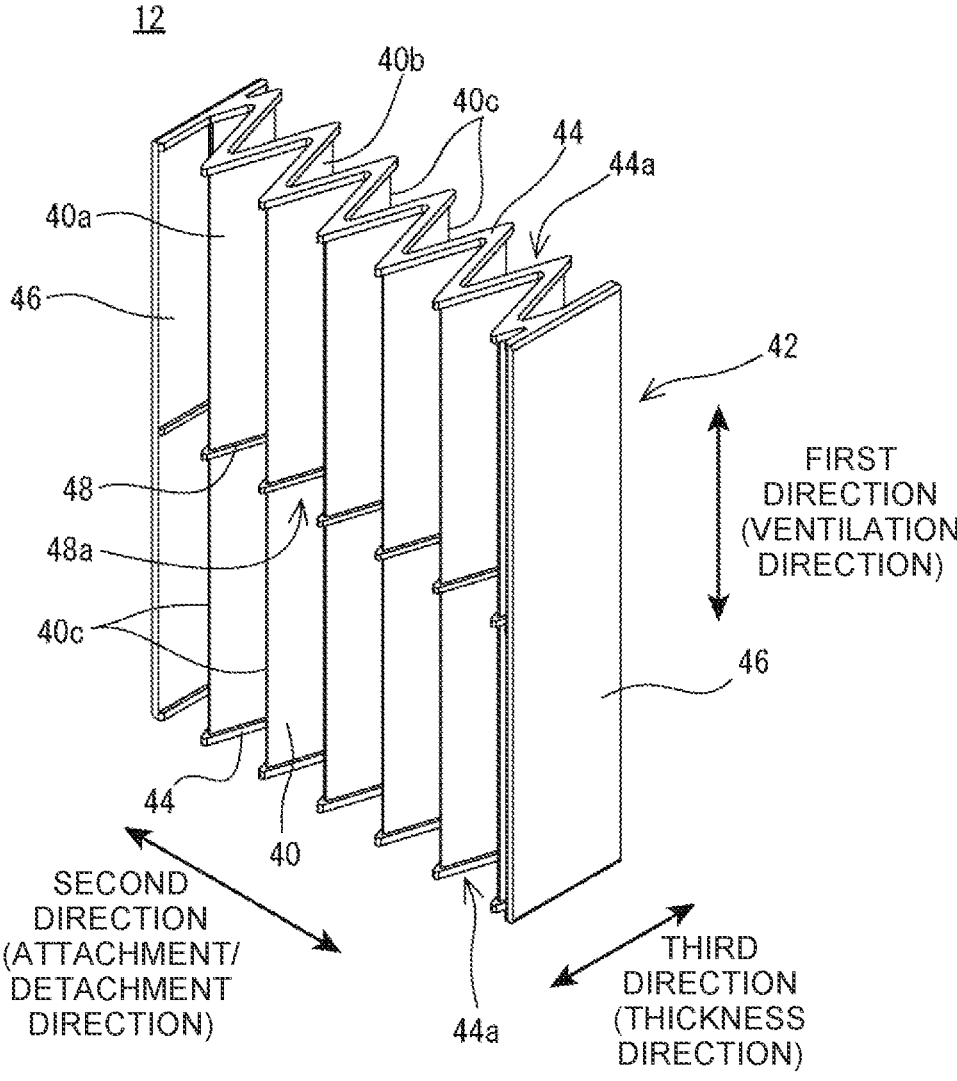
FIG. 4 is a perspective diagram illustrating a filter unit.

Next, a configuration of the filter unit 12 will be described. As illustrated in FIG. 4, the filter unit 12 includes the photocatalytic filter 40 and the rectangular holding frame 42 that holds the photocatalytic filter 40. The photocatalytic filter 40 and the holding frame 42 are integrally molded.

The photocatalytic filter 40 is a filter in which a photocatalyst (photocatalyst particle) is carried on a porous base material such as a nonwoven fabric made of a synthetic resin, and has flexibility. The photocatalyst included in the photocatalytic filter 40 is excited by irradiation with light such as ultraviolet light to generate active oxygen species, thereby causing the active oxygen species to remove (sterilize) bacteria contained in the air and to decompose (deodorize) odor components. Known photocatalysts such as titanium dioxide and tungsten oxide may be used as a photocatalyst, and among these, titanium dioxide is more preferably used.

The photocatalytic filter 40 is formed in a wave shape (also referred to as a pleat shape or a bellows shape) in which a hill section 40a and a valley section 40b that extend in a first direction are alternately arranged in a second direction orthogonal to the first direction. In the present embodiment, the photocatalytic filter 40 is formed in a triangular wave shape with folds 40c formed at projecting ends (tops and bottoms) of the hill sections 40a and the valley sections 40b, and a plurality of the folds 40c are formed so as to extend in the first direction. As described above, the photocatalytic filter 40 is formed in a wave shape (as is folded), thereby being capable of preventing the photocatalytic filter 40 from increasing in size and of increasing a contact area between the photocatalytic filter 40 and the air.

The holding frame 42 includes first frames 44 and second frames 46 that hold four sides of the photocatalytic filter 40. The holding frame 42 is formed of an ABS resin or a synthetic resin such as PC/ABS alloy formed by mixing an ABS resin with polycarbonate.

Each of the first frames 44 is a portion for retaining the wave shape of the photocatalytic filter 40 and is provided in the first direction so as to cover both ends of the photocatalytic filter 40. Each of the first frames 44 has an opening 44a (first opening) that causes an air flow to pass in the first direction and is configured so as not to disturb a flow of air generated by the air blowing fan 16. Specifically, each of the first frames 44 is formed in a wave shape extending along the end in the first direction of the photocatalytic filter 40 (that is to say, formed in a wave shape so as to extend in the second direction) and has the opening 44a in a triangular cross shape formed between inclined pieces that form the wave (hills and valleys).

The second frames 46 are provided in the second direction at both ends of the photocatalytic filter 40. Each of the second frames 46 are formed in a rectangular long plate shape extending in the first direction and connects the ends of the first frame 44 to each other. Each of the second frames 46 forms a ventilation passage extending in the first direction, and regulates diffusion of an air flow in the second direction (that is to say, out of a width of the photocatalytic filter 40).

In addition, the holding frame 42 further includes third frames 48 provided so as to sandwich a center in the first direction of the photocatalytic filter 40. Each of the third frame 48 is a portion for retaining the wave shape of the photocatalytic filter 40 in the same manner as each of the first frames 44 and has an opening 48a that causes an air flow to pass in the first direction. In the present embodiment, each of the third frames 48 is formed in a wave shape extending in the second direction along the main surface of the photocatalytic filter 40.

Figure 5:
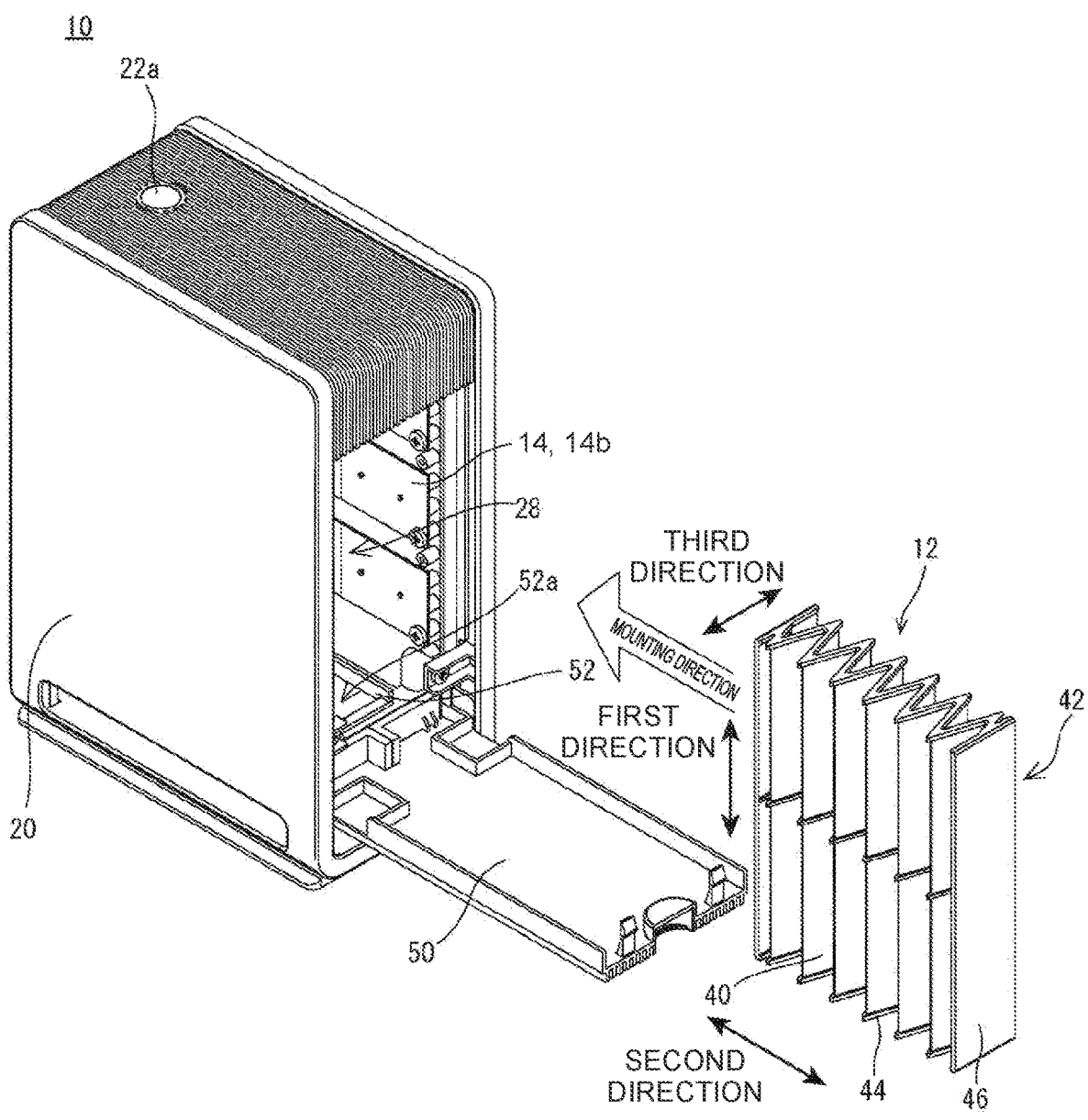
FIG. 5 is a diagram in mounting the filter unit into a housing of the air purifier.

As illustrated in FIG. 5, such a filter unit 12 can be attached to and detached from the unit housing section 28 by opening an opening and closing cover 50 provided at one side surface of the housing 20.

According to the present embodiment, as can be clearly seen in FIG. 2 and FIG. 5, the filter unit 12 (photocatalytic filter 40) is housed in the unit housing section 28 such that an air flow generated by the air blowing fan 16 can flow along the first direction (that is to say, a direction in which each of the folds 40*c* of the photocatalytic filter 40 extends). In other words, the filter unit 12 is vertically housed in the unit housing section 28 so as to make the first direction in a vertical direction, so that the air flow generated by the air blowing fan 16 flows along both main surfaces of the photocatalytic filter 40.

The unit housing section 28 has provided therein a unit guide 52 that guides the filter unit 12 to be attached thereto and be detached therefrom. The filter unit 12 is guided to a mounting position by the unit guide 52. This unit guide 52 includes an opening 52*a* (a second opening), which causes a flow of air to pass in communication with the openings 44*a* of the first frames 44 in the first direction, and is configured so as not to disturb a flow of air generated by the air blowing fan 16. Specifically, there is provided a pair of unit guides 52 that is disposed on an upper end and a lower end, respectively of the unit housing section 28 in a thickness direction of the filter unit 12 (a third direction orthogonal to the first direction and the second direction) and at a predetermined interval and that extends in an attachment/detachment direction (the second direction) of the filter unit 12. Each of the unit guides 52 is formed in a cross-sectional L-shape and slidably supports the first frames 44, which are included in the filter unit 12. The opening 52*a* is formed between the pair of unit guides 52, and therefore, is in communication with the openings 44*a* in a state where the filter unit 12 is mounted in the unit housing section 28.

With regard to the air purifier 10 as described above, when the power button 22*a* is turned on, the controller 100 drives the air blowing fan 16 as well as turns on the light source 14 (LED 32), and then, irradiates each of the main surfaces of the photocatalytic filter 40 with light. In accompany with driving of the air blowing fan 16, air taken from the air intake port 24 into the housing 20 is firstly absorbed by the activated carbon filter 18 to be removed. Next, the air passed through the activated carbon filter 18 flows upward through the unit housing section 28 along both of the main surfaces of the photocatalytic filter 40. Contact of the photocatalytic filter 40 and the air causes organic substances adhering to the photocatalytic filter 40 to be decomposed with an action of the photocatalyst, thereby resulting in performing sterilization and deodorization. Then, clean air purified by the photocatalytic filter 40 is discharged from the exhaust port 26 to an outside of the housing 20.

In this case, since the photocatalytic filter 40 is formed in a wave shape, thereby causing the contact area between the photocatalytic filter 40 and the air to increase, the air can be efficiently purified. Further, the air is not caused to pass in the thickness direction of the photocatalytic filter 40 but is caused to flow along the main surfaces of the photocatalytic filter 40, thereby enabling a pressure loss to be reduced. In particular, the air is caused to flow along the first direction in which the hill sections 40*a* and the valley sections 40*b* of the photocatalytic filter 40 extend thus to be capable of reduce a pressure loss more appropriately. Furthermore, the air is caused to flow along both of the main surfaces of the photocatalytic filter 40, and both of the main surfaces of the photocatalytic filter 40 are irradiated with light by using the first light source 14*a* and the second light source 14*b*. Thus, the air can be purified more efficiently. Moreover, each of the first frames 44 has the opening 44*a* as well as the pair of the unit guides 52 includes the opening 52*a*. Therefore, the air can appropriately flow along both of the main surfaces of the photocatalytic filter 40 so that the first frames 44 and the pair of unit guides 52 do not disturb a flow of the air.

Figure 6:
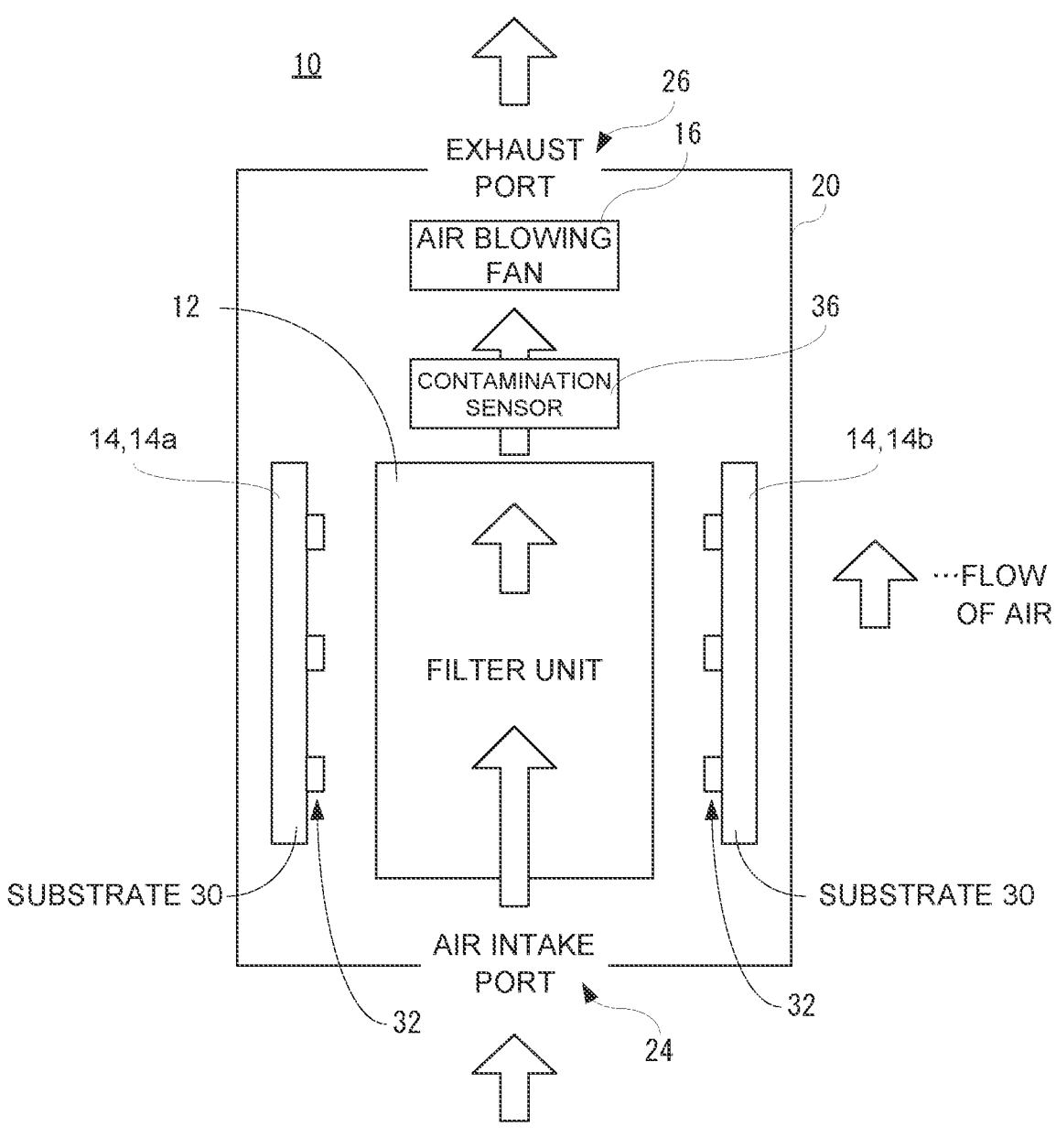
FIG. 6 is a diagram schematically illustrating a structure of the air purifier.

FIG. 6 is a diagram schematically illustrating a structure of the air purifier 10 shown in FIG. 1 to FIG. 5. As illustrated in FIG. 6, the air purifier 10 further includes a contamination sensor 36, and as one example, the contamination sensor 36 is disposed between the filter unit 12 and the air blowing fan 16. However, the contamination sensor 36 may be disposed between the filter unit 12 and the air intake port 24. The contamination sensor 36 is an organic substance sensor (an odor sensor or a VOC sensor) that detects a contamination level.

Figure 7:
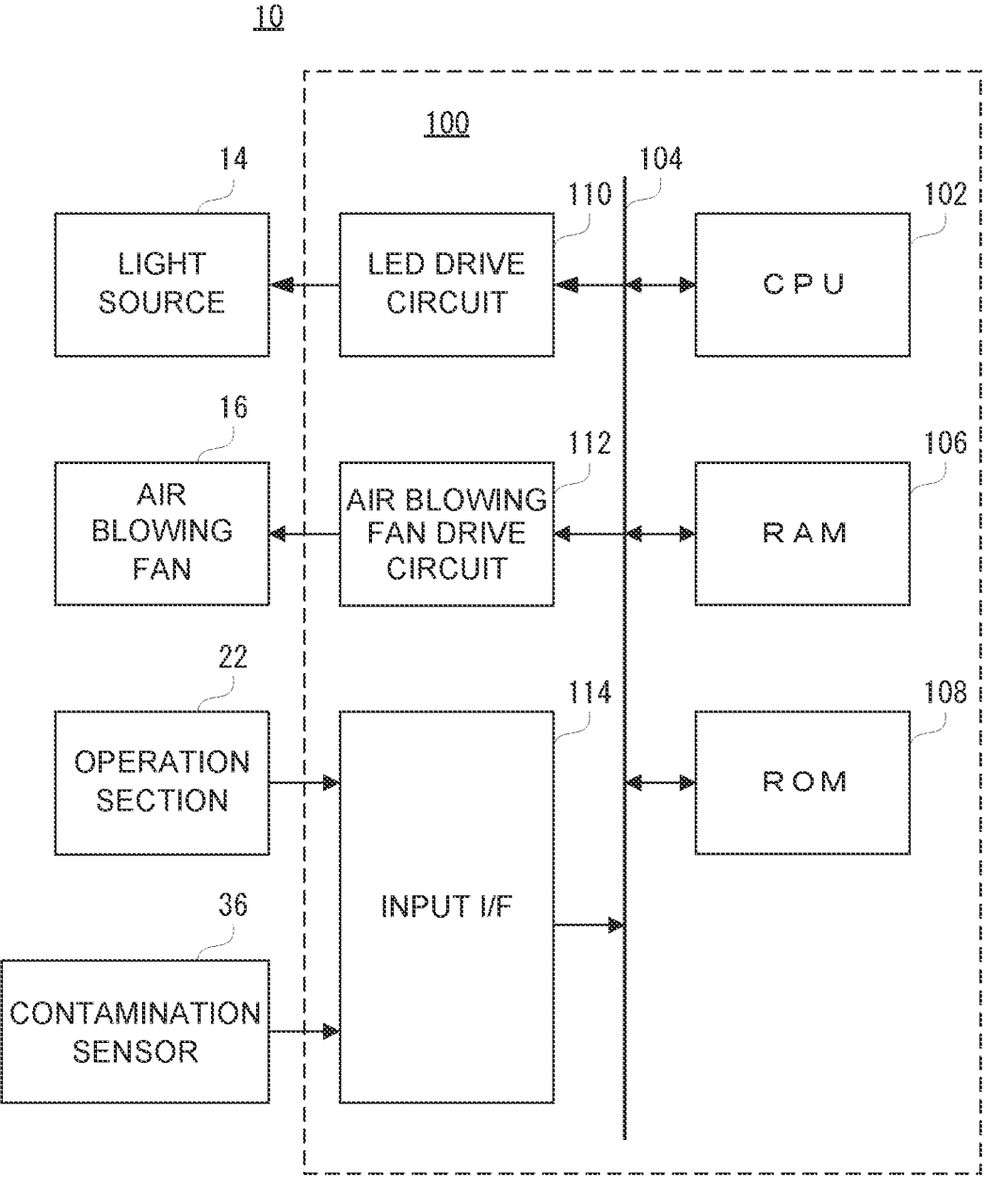
FIG. 7 is a block diagram illustrating an electrical configuration of the air purifier.

FIG. 7 is a block diagram illustrating an electrical configuration of the air purifier 10 according to the first embodiment. As illustrated in FIG. 7, the air purifier 10 is provided with the controller 100 described above. The controller 100 includes a CPU 102, which is connected via a bus 104 to a RAM 106, a ROM 108, a LED drive circuit 110, an air blowing fan drive circuit 112, and an input interface (hereinafter referred to as "input I/F") 114.

In addition, the LED drive circuit 110 is connected to the light source 14, the air blowing fan drive circuit 112 is connected to the air blowing fan 16, and the input I/F 114 is connected to the operation section 22 and the contamination sensor 36.

The CPU 102 is a processor for performing an overall control of the controller 100. The RAM 106 and the ROM 108 are a main storage device of the controller 100. The RAM 106 is used as a work area and a buffer area of the CPU 102. The ROM 108 is an auxiliary storage device of the controller 100, where control program (firmware) is stored. However, the ROM 108 can be a nonvolatile memory such as an EEPROM or a flash memory.

Although not illustrated in drawings, a non-volatile memory such as a HDD, a SSD or a flash memory is provided as an auxiliary storage device in addition to the main storage device.

The LED drive circuit 110 is a circuit for driving the light source 14 (a plurality of LEDs 32) under direction of the CPU 102. The air blowing fan drive circuit 112 is a circuit for driving the air blowing fan 16 under the direction of the CPU 102.

The input I/F 114 outputs operation signals input from the operation section 22 to the CPU 102 and detection values (that is to say, voltage values) that are input from the contamination sensor 36 to the CPU 102.

As described above, the air purifier 10 operates in any one of the operating modes for air purification that comprises a silent mode, a normal mode, and a strong mode. The air purifier 10 decomposes organic substances (organic compounds) adhering to the photocatalytic filter 40 by irradiating the photocatalytic filter 40 with light in addition to flowing the air taken from the outside along the main surface (surface) of the photocatalytic filter 40, thereby purifying the air.

Figure 8:
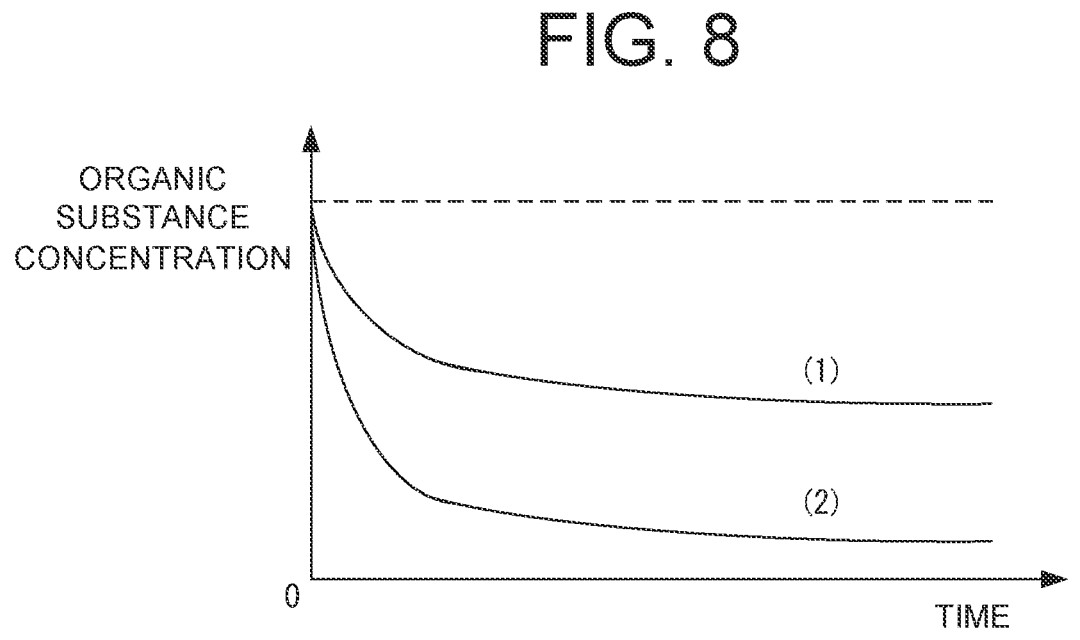

FIG. 8 is a graph illustrating temporal changes in concentration of organic substances in the air, in which a curved line (1) shows temporal changes in concentration of organic substances in the air in a case where there are organic substances excessively adhering to the photocatalytic filter 40 (excessively contaminated) while a curved line (2) shows temporal changes in concentration of organic substances in the air in a case where there are a few organic substances adhering to the photocatalytic filter 40 or there is no organic substance adhering thereto (little contaminated or not contaminated).

As illustrated in FIG. 8, when organic substance excessively adheres to the photocatalytic filter 40, it is difficult to decrease the organic substance concentration in the air even after a certain time has passed in comparison with a case where there are a few organic substances adhering to the photocatalytic filter 40. In other words, a state where organic substances excessively adheres to the photocatalytic filter 40 results in reducing decomposition efficiency or decomposition speed by photocatalysts.

Therefore, according to the first embodiment, in a case where it is determined that a degree to which organic substances has adhered to the photocatalytic filter 40 (that is to say, contamination level) is excessive, the air purifier 10 is designed to operate in a refresh operating mode (hereinafter referred to as a "refresh mode") for decomposing organic substances adhering to the photocatalytic filter 40 so as to reduce contamination of the photocatalytic filter 40. In the refresh mode, the light source 14 is driven at a duty ratio of 100% and the air blowing fan 16 is driven at a duty ratio of 25% or less (25% according to this first embodiment). However, in the refresh mode, an air speed may be set to 0, which means that the air blowing fan 16 may be stopped. In other words, the duty ratio may be set to 0% for the air blowing fan 16. In other words, it may be the slowest one of the speeds of air generated during operation of the air purifier 10. In addition, the duty ratio applied to the light source 14 does not have to be 100%, but may be, for example, 90%, as long as it is the largest one of the light quantities emitted during operation of the air purifier 10.

FIG. 9 is an example of a table showing a criterion of a contamination level. As illustrated in FIG. 9, the table of the criterion of a contamination level describes contamination values for contamination levels. As one example, the contamination levels are evaluated on a three level scale of 0 to 2. The larger the number is, the more contaminated it indicates. As mentioned above, the contamination sensor 36 is a VOC sensor of a semiconductor type. The higher concentration of gas in the air gets, the more a resistance value of the sensor changes, and air contamination is calculated by the changes in the sensor's resistance value from the time when the air is clean as a reference. In other words, clean air condition (no VOC detected) is set to 1, and if detected concentration becomes higher, the value that has been internally processed in accordance with air contamination is output so as to be closer to 0 in a range (voltage value) of 0 or more and 1 or less. This output value is called a contamination value. In a case where the contamination value is 0.65 or more and 1 or less, the contamination level is 0. In a case where the contamination value is 0.35 or more and less than 0.65, the contamination level is 1. In a case where the contamination value is 0 or more and less than 0.35, the contamination level is 2. According to the first embodiment, in a case where the contamination level is 2, it is determined that organic substances excessively adheres to the photocatalytic filter 40 (that is to say, contaminated), the air purifier 10 is designed to operate in the refresh mode for a second predetermined period of time (10 minutes in the first embodiment).

It is noted that the graph illustrated in FIG. 8 defines the curved line (1) as a curved line in a case where the contamination level is 2 and the curved line (2) as a curved line in a case where the contamination level is 0.

According to the first embodiment, processing is performed for checking contamination of the photocatalytic filter 40, in order to operate the air purifier 10 in the refresh mode in a case where the photocatalytic filter 40 is excessively contaminated (check processing for filter contamination, which will be described below). However, processing to determine whether check processing for filter contamination will be performed (determination processing for performing check, which will be described below) is carried out when a power of the air purifier 10 is turned on or periodically (according to the first embodiment, every 30 minutes) when the air purifier 10 is operating. In other words, since it is not possible to determine whether there are many or few organic substance adhering to the photocatalytic filter 40 unless concentration of organic substances in the air sucked by the air blowing fan 16 is high to a certain degree, the determination processing for performing check is carried out in advance to determine whether the check processing for filter contamination should be performed.

In the check processing for filter contamination, the air blowing fan 16 is driven under a condition of a predetermined air speed. In the first embodiment, the air blowing fan 16 is driven at a duty ratio of 50%. In a state where the air blowing fan 16 is driven, the light source 14 is driven at a first light quantity. According to the first embodiment, each of the plurality of the LEDs 32 is driven at a duty ratio of 60%. Here, the first light quantity is 0, which means that the light source 14 may be turned off. In a state where the light source 14 is driven at the first light quantity, a detection value of the contamination sensor 36 is obtained every second, and an average value of the detection values corresponding to a first predetermined number of times (10 times according to the first embodiment) is stored as a first contamination value. In other words, the light source 14 is driven at a first light quantity for a first predetermined period of time (ten seconds in the first embodiment), an average value of detected results corresponding to the first predetermined number of times is stored as the first contamination value. However, one second and 10 times are examples, but need not be limited. The same applies to the second contamination value described below.

Next, the light source 14 is driven at a second light quantity larger than the first light quantity. In the first embodiment, each of the plurality of LEDs 32 is driven at a duty ratio of 80%. In a state where the light source 14 is driven at the second light quantity, a detection value of the contamination sensor 36 is obtained every second, and an average value of the detection values corresponding to the first predetermined number of times is stored as a second contamination value. Here, the light source 14 is driven at the second light quantity that is larger than the first light quantity for a first predetermined period of time to obtain detection values, and an average value of detected results corresponding to the first predetermined number of times is stored as the second contamination value.

It is determined whether detection and processing have been performed to calculate the first contamination value and the second contamination value for a second predetermined number of times (five times according to the first embodiment). The reason for setting the second predetermined number of times to a plurality of times is to enhance a detection accuracy. However, the second predetermined number of times may be one. When the first contamination value and the second contamination value are calculated for the second predetermined number of times, a difference between the first contamination value and the second contamination value (first difference) is calculated for each time, and it is determined whether the first difference that is smaller than a first determination value (according to the first embodiment, the contamination value is 0.3) has been detected for a third predetermined number of times or more (three times according to the first embodiment).

As illustrated in FIG. 8, since a state where organic substances excessively adheres to the photocatalytic filter 40 results in reducing decomposition efficiency or decomposition speed by photocatalysts, few changes can be found in organic substance concentration in the air in a case where the light source 14 is driven at the first light quantity or in a case where the light source 14 is driven at the second light quantity.

Here, the first determination value is decided within a range of contamination values that are at the same contamination level. As illustrated in FIG. 9, in a case where the contamination level is 0 and 2, a range of the contamination value is 0.35. In a case where the contamination level is 1, a range of the contamination value is 0.3. Therefore, in the first embodiment, the first determination value is set to a voltage value equivalent to a range of the contamination value that is 0.3.

In addition, the third predetermined number of times is greater than half of the second predetermined number of times and is decided for the second predetermined number of times or less. This is because if the third predetermined number of times is greater than half of the second predetermined number of times, it can be a high degree of certainty that there is few changes in organic substance concentration in the air. However, in a case where the second predetermined number of times is 1, the third predetermined number of times is also 1.

In a case where the first difference that is smaller than the first determination value has been detected for the third predetermined number of times or more, the air blowing fan 16 and the light source 14 are driven in the refresh mode for the second predetermined period of time.

In other words, according to the first embodiment, it is determined with one contamination sensor 36 whether the photocatalytic filter 40 is excessively contaminated on the basis of changes in organic substance concentration in case of irradiating the photocatalytic filter 40 with different light quantities, and in a case where the photocatalytic filter 40 is excessively contaminated, the air purifier 10 operates in the refresh mode to refresh the photocatalytic filter 40. In other words, decomposition of organic substances adhering to the photocatalytic filter 40 is promoted, and decomposition efficiency or decomposition speed is restored.

FIG. 10 is one example of a table illustrating information on an operating control (hereinafter referred to as a "operating control table"). As illustrated in FIG. 10, the information on an operating control sets an illuminance and an air speed for each operating mode. As one example, there are four operating modes comprising a silent mode, a normal mode, a strong mode, and a refresh mode. Since each mode is described above, redundant descriptions are omitted. As one example, the operating control table is stored in the ROM 108. When an operating mode is decided, the operating control table that has been stored in the ROM 108 is referred to, and the drive of light source 14 and the air blowing fan 16 is controlled in accordance with the operating mode.

However, an illuminance indicates a duty ratio in a case of driving the light source 14, and an air speed indicates a duty ratio in a case of driving the air blowing fan 16.

Figure 11:
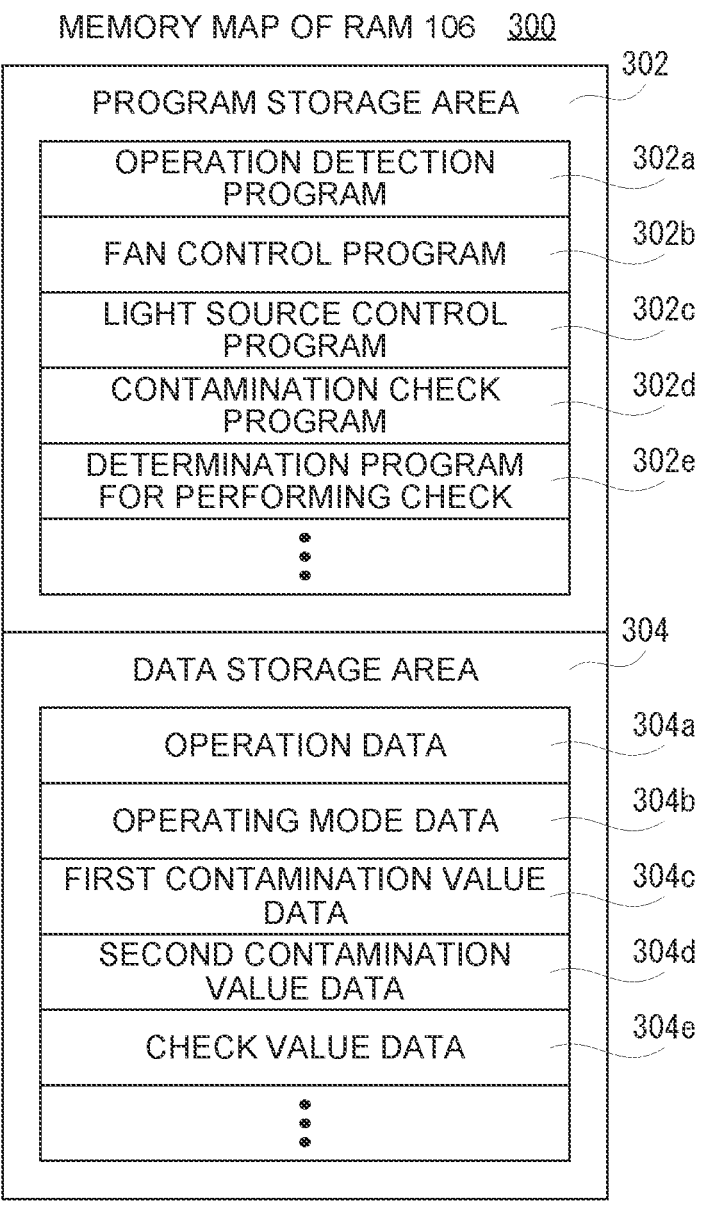
FIG. 11 is a diagram illustrating a memory map of a RAM illustrated in FIG. 7.

FIG. 11 is a diagram illustrating one example of a memory map of the RAM 106 illustrated in FIG. 7. As illustrated in FIG. 11, the RAM 106 includes a program storage area 302 and a data storage area 304. The program storage area 302 stores a control program according to the first embodiment that is executed by the CPU 102 of the air purifier 10.

The control program includes an operation detection program 302a, a fan control program 302b, a light source control program 302c, a contamination check program 302d, and a determination program for performing check 302e.

The operation detection program 302a is a program for detecting operation signals input from the operation section

22 to store the corresponding operation data 304a in the data storage area 304. The fan control program 302b is a program for controlling a drive of the air blowing fan 16 in accordance the operating mode. The light source control program 302c is a program for controlling lighting of the plurality of the LEDs 32 included in the light source 14 in accordance with the operating mode.

The contamination check program 302d is a program for checking contamination level of the photocatalytic filter 40 and shifting the operating mode to the refresh mode if necessary. The determination program for performing check 302e is a program for determining whether to perform the contamination check program 302d.

Although is not illustrated in drawings, the program storage area 302 also stores other programs required for controlling the air purifier 10.

The data storage area 304 stores the operation data 304a, the operating mode data 304b, first contamination value data 304c, second contamination value data 304d, and check value data 304e.

Operation data 304a is data corresponding to the operation signals detected in accordance with the operation detection program 302a. The operating mode data 304b is data for identifying an operating mode set at present and is identification information for a silent mode, a normal mode, a strong mode, or a refresh mode.

The first contamination value data 304c is data of the first contamination value to be calculated on the basis of a detection value of the contamination sensor 36 during execution of the contamination check program 302d in a case of driving the air blowing fan 16 under a condition of a predetermined air speed as well as irradiating the photocatalytic filter 40 with light at the first light quantity.

The second contamination value data 304d is data of the second contamination value to be calculated on the basis of a detection value of the contamination sensor 36 during execution of the contamination check program 302d in a case of driving the air blowing fan 16 under a condition of a predetermined air speed as well as irradiating the photocatalytic filter 40 with light at the second light quantity larger than the first light quantity.

The check value data 304e is data about check values to determine whether to perform the check processing for filter contamination during execution of the determination program for performing check program 302e.

Although not illustrated in drawings, the data storage area 304 also stores other data, flags and timers (not illustrated) required to control the air purifier 10.

Figure 12:
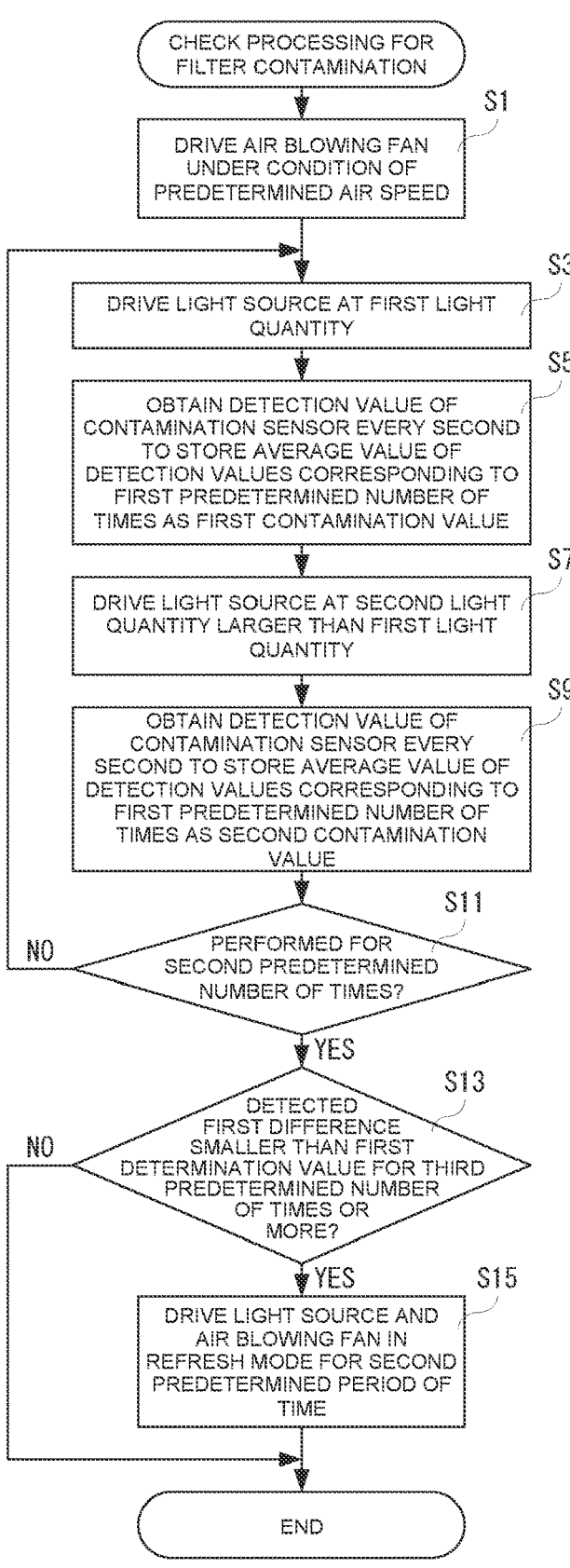
FIG. 12 is a flow diagram illustrating check processing for filter contamination by a CPU that is illustrated in FIG. 7.
Figure 13:
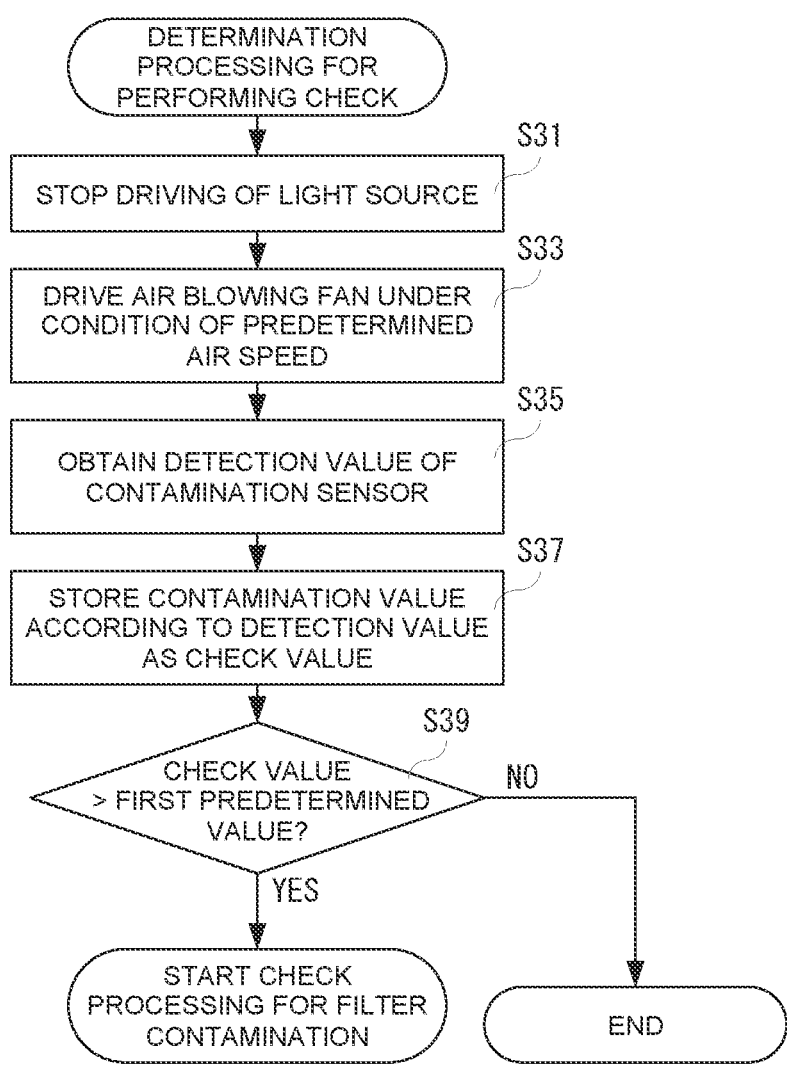
FIG. 13 is a flow diagram illustrating determination processing for performing check by the CPU that is illustrated in FIG. 7.

FIG. 12 is a flow diagram illustrating check processing for filter contamination by the CPU 102 that is illustrated in FIG. 7. FIG. 13 is a flow diagram illustrating determination processing for performing check by the CPU 102 that is illustrated in FIG. 7. In a case where the determination processing for performing check illustrated in FIG. 13 has determined that the check processing for filter contamination will be carried out, the check processing for filter contamination shown in FIG. 12 is initiated.

As illustrated in FIG. 12, the CPU 102 drives the air blowing fan 16 under a condition under a predetermined air speed in step S1 when starting the filter contamination check processing. Here, the CPU 102 controls the air blowing fan drive circuit 112 to drive the air blowing fan 16 at a duty ratio of 50%.

In a next step S3, the light source 14 is driven at the first light quantity. Here, the CPU 102 controls the LED drive circuit 110 to drive each of the plurality of the LEDs 32 at a duty ratio of 60%.

Subsequently, in a step S5, a detection value of the contamination sensor 36 is obtained every second, and an average value of the first predetermined number of times (for example, 10 times) is stored as the first contamination value. In other words, the CPU 102 stores the first contamination value data 304c in the data storage area 304. The reason for setting the first predetermined number of times to a plurality of times is to enhance a detection accuracy.

Next, in a step S7, the light source 14 is driven at the second light quantity larger than the first light quantity. Here, the CPU 102 controls the LED drive circuit 110 to drive each of the plurality of the LEDs 32 at a duty ratio of 80%.

Subsequently, in a step S9, a detection value of the contamination sensor 36 is obtained every second, and an average value of the first predetermined number of times is stored as the second contamination value. In other words, the CPU 102 stores the second contamination value data 304d in the data storage area 304.

In a step S11, it is determined whether processing of the step S3 to the step S9 has been performed for the second predetermined number of times (for example, five times). If the step S11 shows "NO", which is in a case where the processing of the step S3 to the step S9 has not been performed for the second predetermined number of times, the processing returns to the step 3.

On the other hand, if the step S11 shows "YES", which is in a case where the processing of the step S3 to the step S9 has been performed for the second predetermined number of times, in a step S13, it is determined whether the first difference that is smaller than the first determination value has been detected for the third predetermined number of times (for example, three times) or more.

If the step S13 shows "NO", which is in a case where first difference that is smaller than the first determination value has not been detected for the third predetermined number of times or more, the check processing for filter contamination ends. On the other hand, if the step S13 shows "YES", which is in a case where the first difference that is smaller than the first determination value has been detected for the third predetermined number of times or more, the light source 14 and the air blowing fan 16 are, in a step S15, driven in the refresh mode for the second predetermined period of time (for example, 10 minutes) to end the check processing for filter contamination.

As described above, the determination processing for performing check that is carried out in advance to determine whether the check processing for filter contamination should be performed is executed when a power of the air purifier 10 is turned on, or is executed periodically (for example, every 30 minutes) when the air purifier 10 is operating.

As illustrated in FIG. 13, in the determination processing for performing check, when the CPU 102 starts the determination processing for performing check, it stops the drive of the light source 14 in a step S31 and drives the air blowing fan under a condition of a predetermined air speed in a step S33. Here, the CPU 102 controls the air blowing fan drive circuit 112 to drive the air blowing fan 16 at a duty ratio of 50%.

In a subsequent step S35, a detection value is obtained, and in a next step S37, a contamination level corresponding to the detection value is stored as a check value. In other words, the CPU 102 stores the check value data 304e in the data storage area 304.

Then, in a step S39, it is determined whether the check value is larger than the first predetermined value. If the step S39 shows "NO", which is in case where the check value is equal to or smaller than the first predetermined value, the determination processing for performing check ends. On the other hand, if the step S39 shows "YES", which is in case where the check value is larger than the first predetermined value, the check processing for filter contamination illustrated in FIG. 12 starts.

As described above, according to the first embodiment, in a case where organic substances excessively adheres to the photocatalytic filter (that is to say, in a case where a detection result of the contamination sensor 36 meets a predetermined condition), the photocatalytic filter is refreshed, thereby resulting in possibly decomposing organic substances that have adhered to the photocatalytic filter to restore decomposition efficiency of the photocatalytic filter. Thus, the air can be purified efficiently. In addition, the photocatalytic filter can be refreshed at an appropriate time.

In addition, according to this first embodiment, detection values of the contamination sensor are compared with each other in a case of irradiating the photocatalytic filter at variable light quantities, thereby enabling a degree to which organic substances has adhered to the photocatalytic filter, which is a contamination level, to be easily recognized.

Second Embodiment

An air purifier 10 according to a second embodiment is equivalent to the air purifier 10 according to the first embodiment except that the air purifier 10 has a contamination sensor 38 further provided between an air intake port 24 and a filter unit 12 therein and is designed to determine whether to set a refresh mode on the basis of detection values of two contamination sensors, and therefore, redundant descriptions are omitted.

Figure 14:
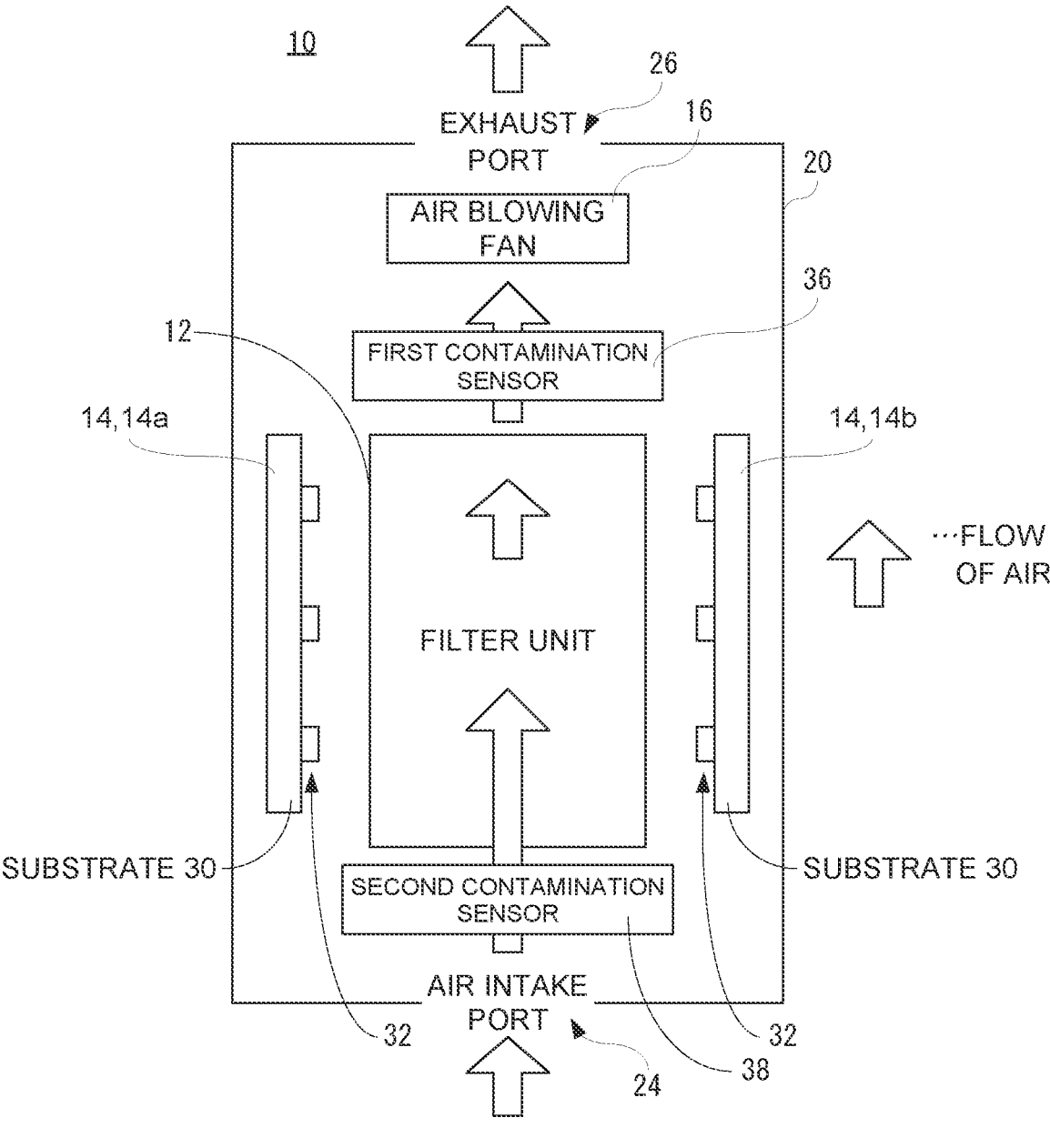
FIG. 14 is a diagram schematically illustrating a structure of an air purifier according to a second embodiment.

FIG. 14 is a diagram schematically illustrating a structure of the air purifier 10 according to the second embodiment. In the second embodiment, since the two contamination sensors are provided, the contamination sensor 36 that is provided between the filter unit 12 and an air blowing fan 16 is called a first contamination sensor 36, and the contamination sensor 38 additionally provided between the air intake port 24 and the filter unit 12 is called a second contamination sensor 38, as illustrated in FIG. 14.

Figure 15:
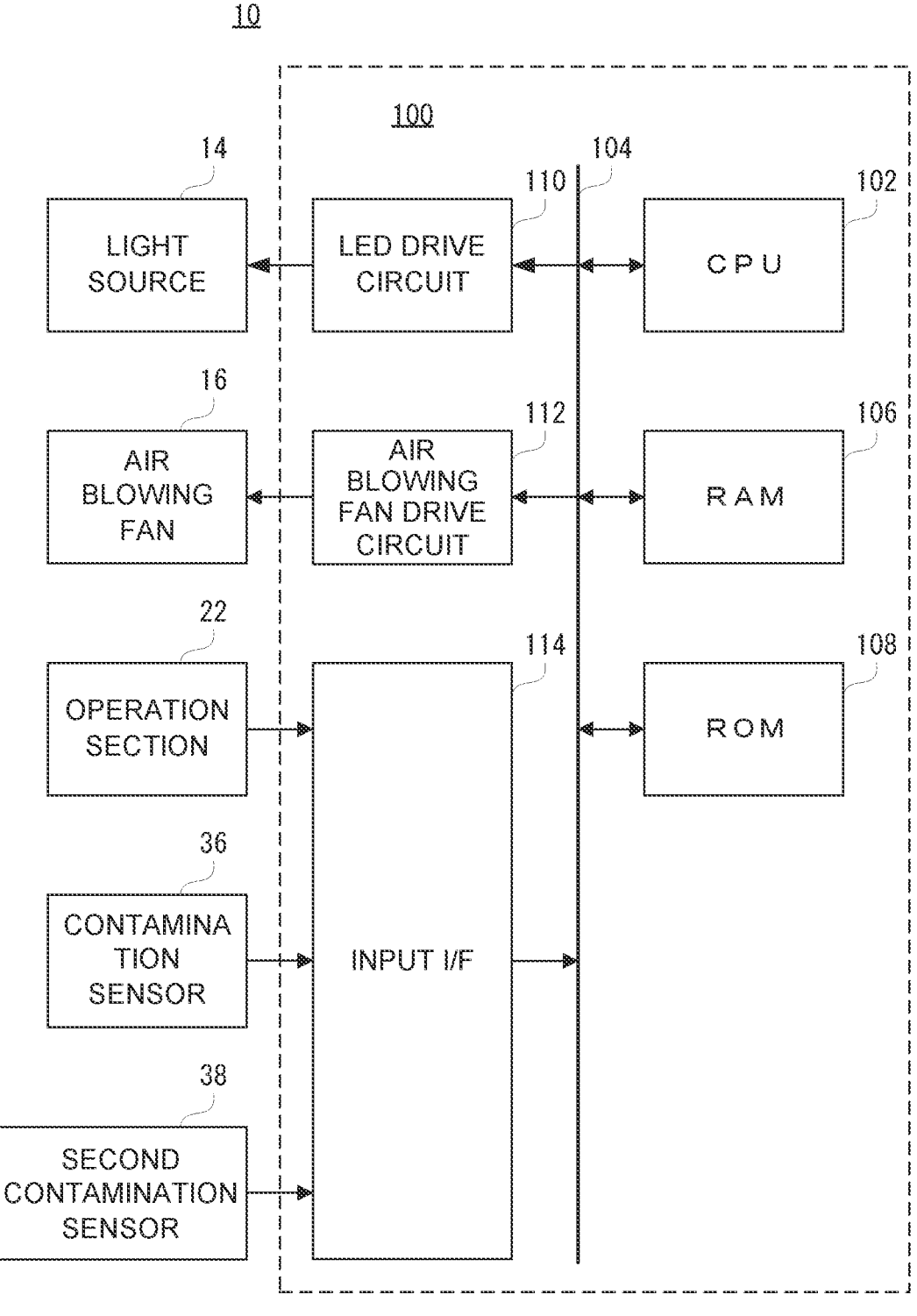
FIG. 15 is a block diagram illustrating an electrical configuration of the air purifier according to the second embodiment.

FIG. 15 is a block diagram illustrating an electrical configuration of the air purifier 10 according to the second embodiment. In the second embodiment, the second contamination sensor 38 is also connected to an input I/F 114.

FIG. 16 is a flow diagram illustrating check processing for filter contamination according to the second embodiment. The check processing for filter contamination according to the second embodiment is described below, but the same portions as the check processing for filter contamination according to the first example will be briefly described.

As illustrated in FIG. 16, when a CPU 102 starts the check processing for filter contamination, the air blowing fan 16 is driven under a condition of a predetermined air speed in a step S61, and it is determined whether a detection value of the second contamination sensor 38 is larger than the second predetermined value in step S63. For example, the second predetermined value is set to a detection value (that is to say, voltage value) of the second contamination sensor 38 corresponding to a contamination value of 0.35.

If a step S63 shows "NO", which is in a case where a detection value of the second contamination sensor 38 is less than the second determination value, the check processing for filter contamination ends. On the other hand, if the step S63 shows "YES", which is in a case where a detection value for the second contamination sensor 38 is larger than the second determination value, the light source 14 and the air blowing fan 16 are, in a step S65, driven under a predetermined condition in a silent mode (refer to FIG. 10) for a third predetermined period of time (for example, 10 seconds).

In a following step S67, a difference between a detection value of the second contamination sensor 38 and a detection value of the first contamination sensor 36 for the third predetermined period of time (referred to as a "second difference" for convenience of description) is calculated and stored. In other words, changes in organic substance concentration in the air before and after sterilization and deodorization that are performed at the photocatalytic filter 40 are calculated.

In a step S69, it is determined whether the processing of the step S65 and the step S67 have been performed for a fourth predetermined number of times (for example, five times). However, the fourth predetermined number of times may be one.

If a step S69 shows "NO", which is in a case where the processing of the step S65 and the S67 has not been performed for the fourth predetermined number of times, the processing returns to the step S65. On the other hand, if the step S69 shows "YES", which is in a case where the processing of the step S65 and the step S67 has been performed for the fourth predetermined number of times, it is determined in a step S71 whether the second difference that is smaller than a second determination value (for example, 0.3) has been detected for a fifth predetermined number of times (for example, three times). In other words, the CPU 102 determines whether the photocatalytic filter 40 is excessively contaminated. It is noted that the second determination value according to the second embodiment is the same as the first determination value according to the first embodiment.

If the step S71 shows "NO", which is in a case where the second difference that is smaller than the second determination value has not been detected for the fifth predetermined number of times, the check processing for filter contamination ends. On the other hand, If the step S71 shows "YES", which is in a case where the second difference that is smaller than the second determination value has been detected for the fifth predetermined number of times, the light source 14 and the air blowing fan 16 are, in step a S73, driven in the refresh mode for a fourth predetermined period of time (for example, 10 minutes) to end the check processing for filter contamination.

It is noted that the determination processing for performing check illustrated in FIG. 13 is equivalent to the determination processing for performing check according to the second embodiment, and therefore, descriptions are omitted. However, the determination processing for performing check may be executed using a detection value of the second contamination sensor 38 instead of a detection value of the first contamination sensor 36.

In the second embodiment, as in the first embodiment, in a case where organic substances excessively adheres to the photocatalytic filter (that is to say, in a case where a difference between a detection result of the first contamination sensor 36 and a detection result of the second contamination sensor 38 meets a predetermined condition), the photocatalytic filter is refreshed, which promotes decomposition of organic substances adhering to the photocatalytic filter, thereby enabling decomposition efficiency of the photocatalytic filter to be restored. Therefore, it is possible to perform sterilization and deodorization efficiently. In addition, the photocatalytic filter can be refreshed at an appropriate time.

According to the second embodiment, in a case where the contamination sensors are provided on an upstream side and a downstream side, respectively, in an air blowing direction by the air blowing fan of the photocatalytic filter, and the photocatalytic filter is irradiated with light at a predetermined light quantity, detection values of the contamination sensors are compared with each other, thereby enabling a degree to which organic substances adhere to the photocatalytic filter, which is a contamination level, to be easily recognized.

Third Embodiment

An air purifier 10 according to a third embodiment is equivalent to the air purifier 10 according to the first embodiment except that the photocatalytic filter 40 is designed to be refreshed at an operating end of the air purifier 10, regardless of whether or not the photocatalytic filter 40 is contaminated, and therefore, redundant descriptions are omitted.

The air purifier 10 according to the third embodiment does not need a contamination sensor 36 because it does not matter whether or not the photocatalytic filter 40 is contaminated.

In the third embodiment, the air purifier 10 decides a fifth predetermined period of time to operate in a refresh mode in accordance with an operating time in a silent mode, a normal mode or a strong mode. As one example, in a case where the operating time in the silent mode, the normal mode, or the strong mode is less than 3 hours, the operating time in the refresh mode (that is to say, the fifth predetermined period of time) is decided to be 10 minutes. In addition, in a case where the operating time in the silent mode, the normal mode, or the strong mode is 3 hours or more and less than 6 hours, the operating time in the refresh mode is set to 20 minutes. Furthermore, in a case where the operating time in the silent mode, the normal mode, or the strong mode is 6 hours or more, the operating time in the refresh mode is set to 30 minutes.

Figure 17:
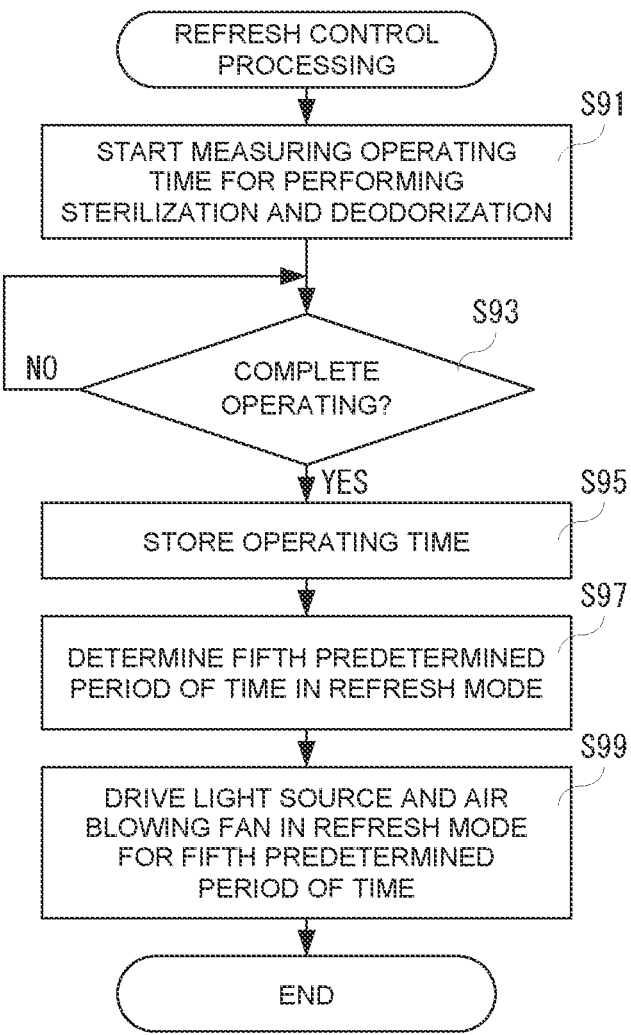
FIG. 17 is a flow diagram illustrating refresh control processing by a CPU of an air purifier according to a third embodiment.

FIG. 17 is a flow diagram illustrating refresh control processing according to the third embodiment. This refresh control processing is initiated when the air purifier 10 starts operating in an operating mode for sterilization and deodorization. As illustrated in FIG. 17, when the CPU 102 starts the refresh control processing, it begins measuring the operating time in the operating mode for sterilization and deodorization in a step S91. In a subsequent step S93, it is determined whether the air purifier 10 ends operating in the operating mode for sterilization and deodorization. If the step S93 shows "NO", which is not at an end of the operating, the processing returns to the step S93. On the other hand, if the step S93 shows "YES", which is at an end of operating, the operating time is stored in a step S95.

In a next step S97, the fifth predetermined period of time for the refresh mode is decided in accordance with the stored operating time. Then, in a step S99, the light source 14 and the air blowing fan 16 are driven in the refresh mode for the fifth predetermined time, and the refresh control processing is completed.

According to this third embodiment, the photocatalytic filter is refreshed at an end of the operating mode for sterilization and deodorization, and therefore, organic substances adhering to the photocatalytic filter is decomposed, and the decomposition efficiency of the photocatalytic filter can be restored. Thus, as in the first embodiment, sterilization and deodorization can be performed efficiently. In addition, the photocatalytic filter can be refreshed at an appropriate time.

It is noted that the light sources are arranged at both sides of the filter unit in each of the above-mentioned embodiments, and however, the light source may be disposed only at one side of the filter unit. Alternatively, a reflective plate may be disposed at a side where the light source is not disposed.

Furthermore, in each of the above-mentioned embodiments, an air flow flowing upward is generated by the air blowing fan, and however, a flowing direction of the air flow generated by the air blowing fan can be changed appropriately. For example, a filter unit can be horizontally disposed such that an air flow that flows horizontally is generated by an air blowing fan to flow along a first direction. In other words, a disposition direction of the filter unit may be vertical or horizontal. The photocatalytic filter may also be of a filtration type.

It is noted that specific values and specific shapes of the components described above are merely one of examples and can be appropriately changed according to necessity such as specification of the product.

What is claimed is:

1. An air purifier comprising:
an air blowing fan;
a photocatalytic filter that includes a photocatalyst;
a light source that irradiates the photocatalytic filter;
a first sensor that is disposed on a downstream side of the photocatalytic filter, in an air blowing direction of air blown by the air blowing fan, the first sensor being configured to detect organic substances contained in the air, and
a controller configured to:
refresh the photocatalytic filter by causing the light source to emit light at a maximum light quantity that is a largest one of light quantities emitted during operation of the air purifier, and by driving the air blowing fan at a minimum air speed that is a slowest one of air speeds generated during the operation of the air purifier,
perform first check processing to check an amount of organic substances adhering to the photocatalytic filter, the first check processing comprising:
causing the light source to emit light at a first light quantity and obtaining, from the first sensor, a first detection value indicative of a first amount of organic substances contained in the air,
causing the light source to emit light at a second light quantity, different from the first light quantity, and obtaining, from the first sensor, a second detection value indicative of a second amount of organic substances contained in the air, and
calculating a difference between the first detection value and the second detection value, and
determine, based on the calculated difference, whether further refreshing of the photocatalytic filter is necessary.

2. The air purifier according to claim 1, wherein:
the first detection value is an average value of detection results corresponding to a first predetermined number of times, obtained by driving the light source at the first light quantity, for a first predetermined period of time,
the second detection value is an average value of detection results corresponding to the first predetermined number of times, obtained by driving the light source at the second light quantity larger than the first light quantity, for the first predetermined period of time,
the maximum light quantity is larger than the second light quantity, and the light source is caused to emit light at the maximum light quantity in a case that the difference is smaller than a first determination value.

3. The air purifier according to claim 2, wherein
the difference is calculated for a second predetermined number of times that is two or more, and
the photocatalytic filter is refreshed in a case that a number of times that the difference is calculated as smaller than the first determination value is equal to a third predetermined number of times.

4. The air purifier according to claim 1, wherein
the first check processing is performed in a case that an initial detection value of the first sensor is equal to, or more than, a first predetermined value in a state in which the light source is turned off.

5. The air purifier according to claim 1, further comprising:
a second sensor that detects organic substances contained in air on an upstream side of the photocatalytic filter in the air blowing direction by the air blowing fan, wherein
the controller is further configured to perform, in a state in which the light source is caused to emit light at a predetermined light quantity based on a detection value of the second sensor, second check processing for checking contamination of the photocatalytic filter by determining a second difference between a third detection value obtained from the first sensor and a fourth detection value obtained from the second sensor.

6. The air purifier according to claim 5, wherein
the controller refreshes the photocatalytic filter by causing the light source to emit light at the maximum light quantity and driving the air blowing fan at the minimum air speed in a case that the second difference is smaller than a second determined value.

7. The air purifier according to claim 5, wherein
the second check processing is performed in a case that an initial detection value of the first sensor or an initial detection value of the second sensor, in a state in which the light source is turned off, is equal to, or more than, a first predetermined value.

8. The air purifier according to claim 5, wherein
the second difference is calculated for a first predetermined number of times that is two or more, and
the photocatalytic filter is refreshed in a case that a number of times that the second difference is calculated as smaller than the second determination value is equal to a second predetermined number of times.

9. The air purifier according to claim 1, wherein
the controller is configured to refresh the photocatalytic filter when an operation for sterilization and deodorization ends.

10. The air purifier according to claim 9, wherein
the controller is further configured to determine a time at which to refresh the photocatalytic filter based on a time taken for the operation for sterilization and deodorization.

11. The air purifier according to claim 1, wherein the photocatalytic filter is formed in a wave shape in which a hill section and a valley section that extend in a first direction are alternately arranged in a second direction orthogonal to the first direction, and an air flow is generated by the air blowing fan flow along the first direction.

12. A method for controlling an air purifier, the air purifier comprising:

an air blowing fan;

a photocatalytic filter that includes a photocatalyst;

a light source that irradiates the photocatalytic filter; and a first sensor that is disposed on a downstream side of the photocatalytic filter, in an air blowing direction of air blown by the air blowing fan, the first sensor being configured to detect organic substances contained in the air, the method comprising:

refreshing the photocatalytic filter by causing the light source to emit light at a maximum light quantity that is a largest one of light quantities emitted during operation of the air purifier, and by driving the air blowing fan at a minimum air speed that is a slowest one of air speeds generated during the operation of the air purifier;

performing first check processing to check an amount of organic substances adhering to the photocatalytic filter, the first check processing comprising:

causing the light source to emit light at a first light quantity and obtaining, from the first sensor, a first detection value indicative of a first amount of organic substances contained in the air, causing the light source to emit light at a second light quantity different from the first light quantity and obtaining, from the first sensor, a second detection value indicative of a second amount of organic substances contained in the air, and calculating a difference between the first detection value and the second detection value, and determining, based on the calculated difference, whether further refreshing of the photocatalytic filter is necessary.

\* \* \* \* \*